(12) United States Patent
Chang

(10) Patent No.: US 8,933,173 B2
(45) Date of Patent: *Jan. 13, 2015

(54) SURFACE ANTI-BIOMOLECULE AGENT

(75) Inventor: Yung Chang, Tao-Yuan (TW)

(73) Assignee: Chung Yuan Christian University, Tao-Yuan (TW)

( * ) Notice: Subject to any disclaimer, the term of this patent is extended or adjusted under 35 U.S.C. 154(b) by 129 days.

This patent is subject to a terminal disclaimer.

(21) Appl. No.: 12/952,913

(22) Filed: Nov. 23, 2010

(65) Prior Publication Data

US 2012/0128623 A1    May 24, 2012

(51) Int. Cl.
- *A01N 37/44* (2006.01)
- *A01N 41/08* (2006.01)
- *A01N 25/10* (2006.01)

(52) U.S. Cl.
CPC ............... *A01N 37/44* (2013.01); *A01N 41/08* (2013.01)
USPC ........................................ 525/291; 424/78.17

(58) Field of Classification Search
CPC ........ A01N 37/44; A01N 41/08; A01N 25/10

USPC ........................................ 424/78.17; 525/291
See application file for complete search history.

(56) References Cited

U.S. PATENT DOCUMENTS

| | | |
|---|---|---|
| 6,117,417 A | 9/2000 | Wicks et al. |
| 7,713,541 B1 | 5/2010 | Pacetti et al. |
| 2009/0156460 A1* | 6/2009 | Jiang et al. .......... 514/2 |
| 2012/0128600 A1* | 5/2012 | Chang et al. ............ 424/54 |
| 2012/0128775 A1* | 5/2012 | Chang et al. ............ 424/489 |

OTHER PUBLICATIONS

Li et al. Macromolecules, 2003, 36, 8268-8275.*

* cited by examiner

*Primary Examiner* — Mark Kaucher
(74) *Attorney, Agent, or Firm* — WPAT, PC; Justin King

(57) ABSTRACT

This invention discloses a surface anti-biomolecule agent for an artificially or naturally charged substrate. The anti-biomolecule agent comprises a copolymer employing anchoring blocks or domains to binds sites of the substrate via electrostatic attractive force, and employing zwitterionic blocks or domains extended outwardly to reduce the attachment of biomolecules to the substrate.

7 Claims, 17 Drawing Sheets

SURFACE ANTI-BIOMOLECULE AGENT

CROSS-REFERENCE TO RELATED APPLICATIONS

This application relates to co-pending U.S. application Ser. No. 12/953,036 filed Nov. 23, 2010 and entitled "Dental care product"; and relates to U.S. application Ser. No. 12/953,110 filed Nov. 23, 2010 and entitled "Biocarrier and method of using the same." The foregoing applications are commonly assigned and the entire contents of all of them are expressly incorporated herein by reference.

BACKGROUND OF THE INVENTION

1. Field of the Invention

The present invention relates generally to surface anti-biomolecule agents, and, more particularly, to a surface anti-biomolecule agent for an artificially or naturally charged substrate.

2. Description of the Prior Art

Controlling microorganisms such as bacteria, fungi, mold, mildew, and algae on surfaces is necessary in many fields including medical, food, agriculture, industry, and so forth. The mechanism of an antimicrobial action determines how it can be used in surface treatments. Typically the prior art controls the microbial growth via two ways: (1) by killing microorganisms or (2) by inhibiting the growth of microorganisms. Physical or chemical agents are used for either killing or preventing the growth of microorganisms. Agents that kill cells are called "-cidal" agents; agents that inhibit the growth of cells (without killing them) are called as "-static" agents.

Most conventional antimicrobial agents were either poisons or heavy metals, typically containing antibiotics, phenols, iodine, quaternary ammonium compounds, or heavy metals, which are harmful not only to microorganisms, but also to humans, the treated surface, and the environment. In addition, poisons or heavy metals cannot kill the microbe completely, allowing the microbe survive, change, and become resistant to the poisons or heavy metals.

Replacing heavy metals and toxins, antimicrobial nanotechnology is a "mechanical kill" that eliminates the microbes from changing and adapting into superbugs. The antimicrobial nanotechnology have the advantages of long lasting and beneficial to the environment, but it may cannot be used in some medical applications.

Therefore, it would be advantageous to develop novel mechanisms and antimicrobial agents for effectively controlling microorganisms.

SUMMARY OF THE INVENTION

The present invention relates to surface anti-biomolecule agents for an artificially or naturally charged substrate.

One embodiment provides a surface anti-biomolecule agent for an artificially or naturally charged substrate, comprising a biomolecule resistance block copolymer, with a zwitterionic block and an anchoring block with at least a sub-block having a first electricity, wherein the sub-block having the first electricity binds to sites, on the charged surfaces, having a second electricity opposite to the first electricity, and the zwitterionic block extends outwardly to reduce the attachment of biomolecules to the charged substrate.

Another embodiment provides a surface anti-biomolecule agent for an artificially or naturally charged substrate, comprising a biomolecule resistance random copolymer, with a zwitterionic domain and an anchoring domain with a sub-domain having a first electricity, wherein the sub-domain having the first electricity binds to sites, on the charged surfaces, having a second electricity opposite to the first electricity, and the zwitterionic domain extends outwardly to reduce the attachment of biomolecules to the charged substrate.

Another embodiment provides a surface anti-biomolecule agent for an artificially or naturally charged substrate, comprising a biomolecule resistance copolymer, with a anchoring main chain and a zwitterionic pendant group or zwitterionic side chain, the anchoring main chain having a sub-block or a sub-domain having a first electricity, wherein the sub-block or the sub-domain having the first electricity binds to sites, on the charged surfaces, having a second electricity opposite to the first electricity, and the zwitterionic pendant group or zwitterionic side chain extends outwardly to reduce the attachment of biomolecules to the charged substrate.

DESCRIPTION OF THE PREFERRED EMBODIMENT

Reference will now be made in detail to specific embodiments of the invention. Examples of these embodiments are illustrated in accompanying drawings. While the invention will be described in conjunction with these specific embodiments, it will be understood that it is not intended to limit the invention to these embodiments. On the contrary, it is intended to cover alternatives, modifications, and equivalents as may be included within the spirit and scope of the invention as defined by the appended claims. In the following description, numerous specific details are set forth in order to provide a through understanding of the present invention. The present invention may be practiced without some or all of these specific details. In other instances, well-known process operations and components are not been described in detail in order not to unnecessarily obscure the present invention. While drawings are illustrated in details, it is appreciated that the quantity of the disclosed components may be greater or less than that disclosed, except expressly restricting the amount of the components.

The present invention relates to surface anti-biomolecule agents with high degree of biomolecule resistance. The surface anti-biomolecule agents of this invention are used in artificially or naturally charged substrates, for reducing the attachment of biomolecules, such as bacteria, fungi, mold, mildew, algae, plankton, planarian, viruses, and so on, to the charged substrates.

The anti-biomolecule agent comprising a copolymer employing anchoring blocks or domains to binds sites of the substrate via electrostatic attractive force (hydrophobic interaction may coexist in some cases), and employing zwitterionic blocks or domains extended outwardly to reduce the attachment of biomolecules to the substrate. To this end, the sites or surface of the substrate should be naturally charged or artificially charged.

In one example, an external electric field is applied on the substrate to have the substrate positively charged, negatively charged, or uncharged, accordingly. Therefore, the anti-biomolecule agents may attach to the substrate when external electric field is on, and detach from the substrate when external electric field is off, so as to provide a smart coating material.

Figure 8:
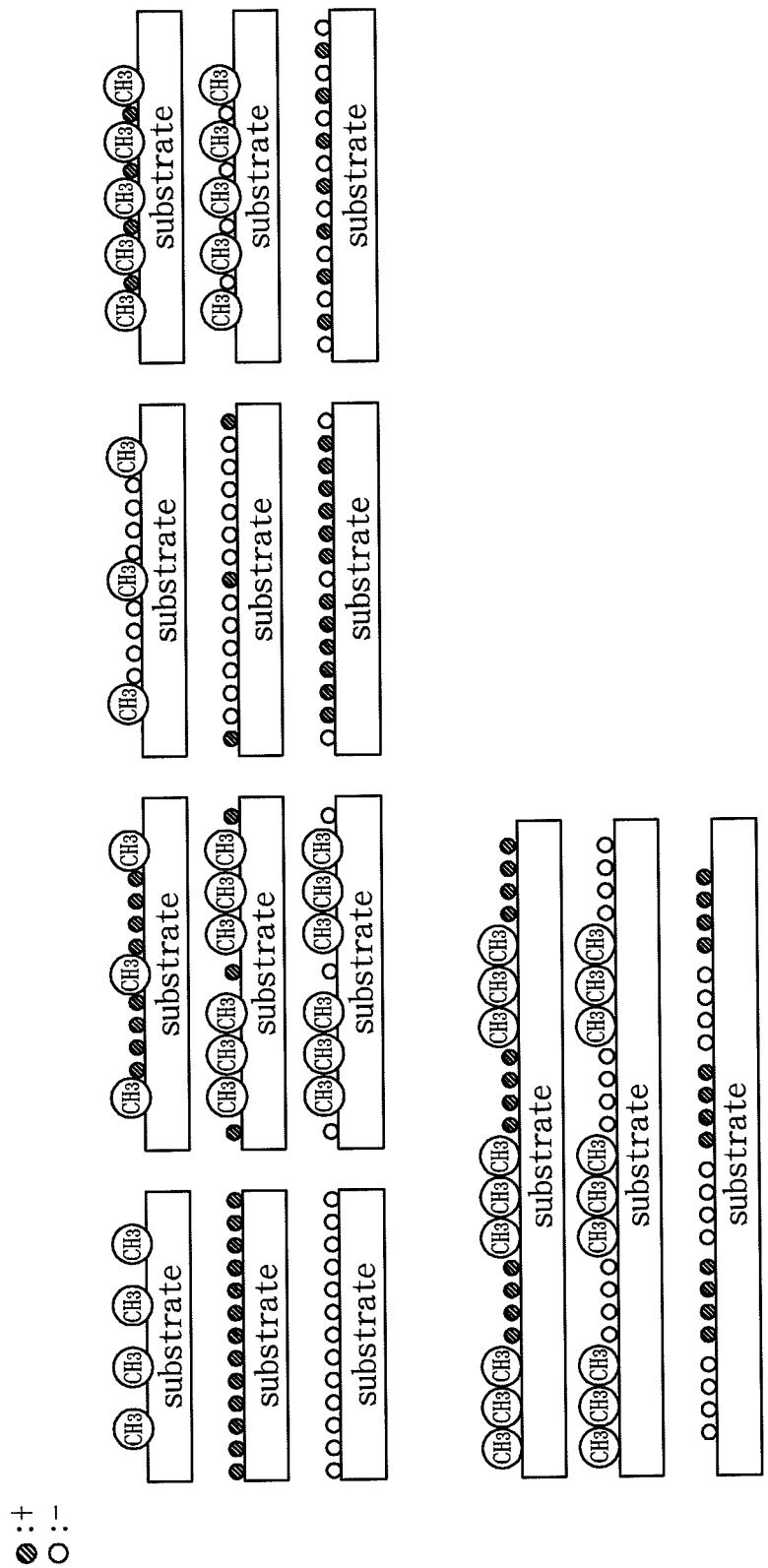
FIG. 8 illustrates substrates with various patterns that can be treated by the anti-biomolecule agents of this invention.

FIG. 8 illustrates some substrates that can be treated by the anti-biomolecule agent of this invention, where positive charged sites, negative charged sites, hydrophobic sites, or combination thereof constitute various distributed patterns on the substrate.

The anti-biomolecule agent of this invention may be used in any substrate with various morphologies of any fields such as medical, food, agriculture, industry, and so forth, as long as the above-mentioned mechanism can be applied. Such substrates may include metal, ceramics, polymer, glass, composite material, human hard tissue such as bone, teeth, medical implanted device, etc.

Method for coating the anti-biomolecule agents of this invention on substrates may comprise manual coating, spin coating, dip coating, spray coating, roller coating, and other suitable methods as those conventionally used for preparing antimicrobial surfaces. Typically the anti-biomolecule agents of this invention are solvable in water and are coated on the substrate in a self-assembled manner using the above-mentioned mechanism.

The anti-biomolecule agents of this invention is preferably water-based; it may also be formulated as powders, gels, foams, pastes, liquid concentrate, or tablets, using standard formulations known in the art, if required.

The anti-biomolecule agents of this invention provide safe, unique, long-lasting, and environmentally friendly antimicrobial barriers on treated surfaces against a wide range of microbial contaminants. The following embodiments describe the details of the anti-biomolecule agent of this invention.

One embodiment of this invention provides a surface anti-biomolecule agent used in an artificially or naturally charged substrate. The surface anti-biomolecule agent comprises preferably equal to or more than 0.1 mg/ml of a biomolecule resistance block copolymer, which comprises a zwitterionic block and an anchoring block, which comprises at least a sub-block having a first electricity, wherein the sub-block binds to sites of the charged substrate having a second electricity opposite to the first electricity, and the zwitterionic block extends outwardly to reduce the attachment of biomolecules to the charged substrate.

The anchoring block may further comprise a sub-block having the second electricity, so as to bind to sites of the charged substrate having the first electricity. In this case, both of the anchoring block and the charged substrate have the first electricity and the second electricity, and the ratio of the size of the sub-block having the first electricity to the size of the sub-block having the second electricity is related to the ratio of the number of the sites having the second electricity to the number of the sites having the first electricity.

One or more sub-blocks of the anchoring block is substantially formed by positively charged monomers or negatively charged monomers. The positively charged monomers are derived from the group consisting of the following:

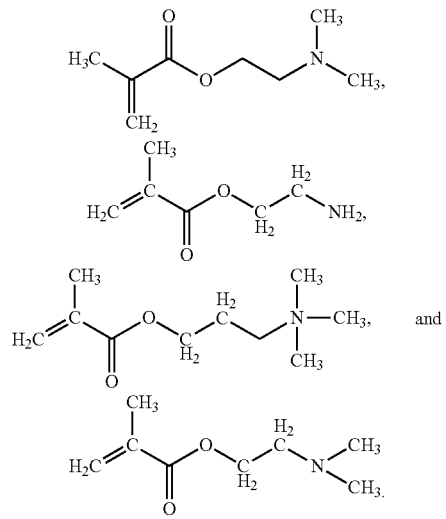

the negatively charged monomers are derived from the group consisting of the following:

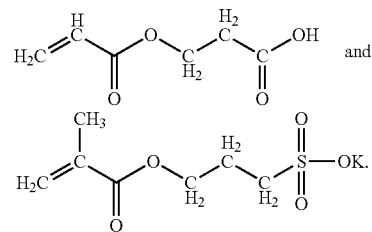

In addition, the charged substrate may further comprise hydrophobic sites. In this case, the anchoring block further comprises at least a sub-block having hydrophobic groups, so as to bind to hydrophobic sites of the charged substrate via hydrophobic interactions. And similarly, the size ratio of the sub-block having the first electricity to the sub-block having hydrophobic groups is related to the number ratio of the sites having the second electricity to the hydrophobic sites.

Preferably, the biomolecule resistance block copolymer is selected from the group consisting of diblock, triblock, multiblock, starblock, and graft block copolymer.

In this text, "an object with a first electricity" refers to "an object is positively charged or negatively charged" or "an object with a positive sign or negative sign of electricity." In this embodiment, the first electricity may be positive electricity or negative electricity.

Preferably, the zwitterionic block is polymerized by a zwitterionic monomer selected from the group consisting of sulfobetaine, carboxylbetaine, derivatives thereof, and combinations thereof. In an example, the zwitterionic monomers are derived from the group consisting of the following:

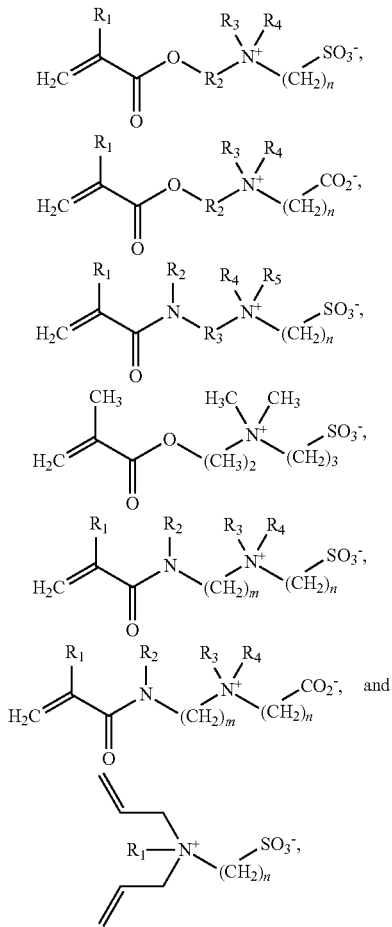

where $R_1$, $R_2$, $R_3$, $R_4$, and $R_5$ are alkyl groups and n, m are integers of 2~5. In another example, the zwitterionic block is polymerized by a zwitterionic unit comprising mix-charged monomers, and the mix-charged monomers comprise mixing two oppositely charged compounds with overall charge neutrality.

In addition, the weight average molecular weight ($M_w$) of the zwitterionic block is preferably equal to or more than 10 kDa.

Figures 1A, 1B:
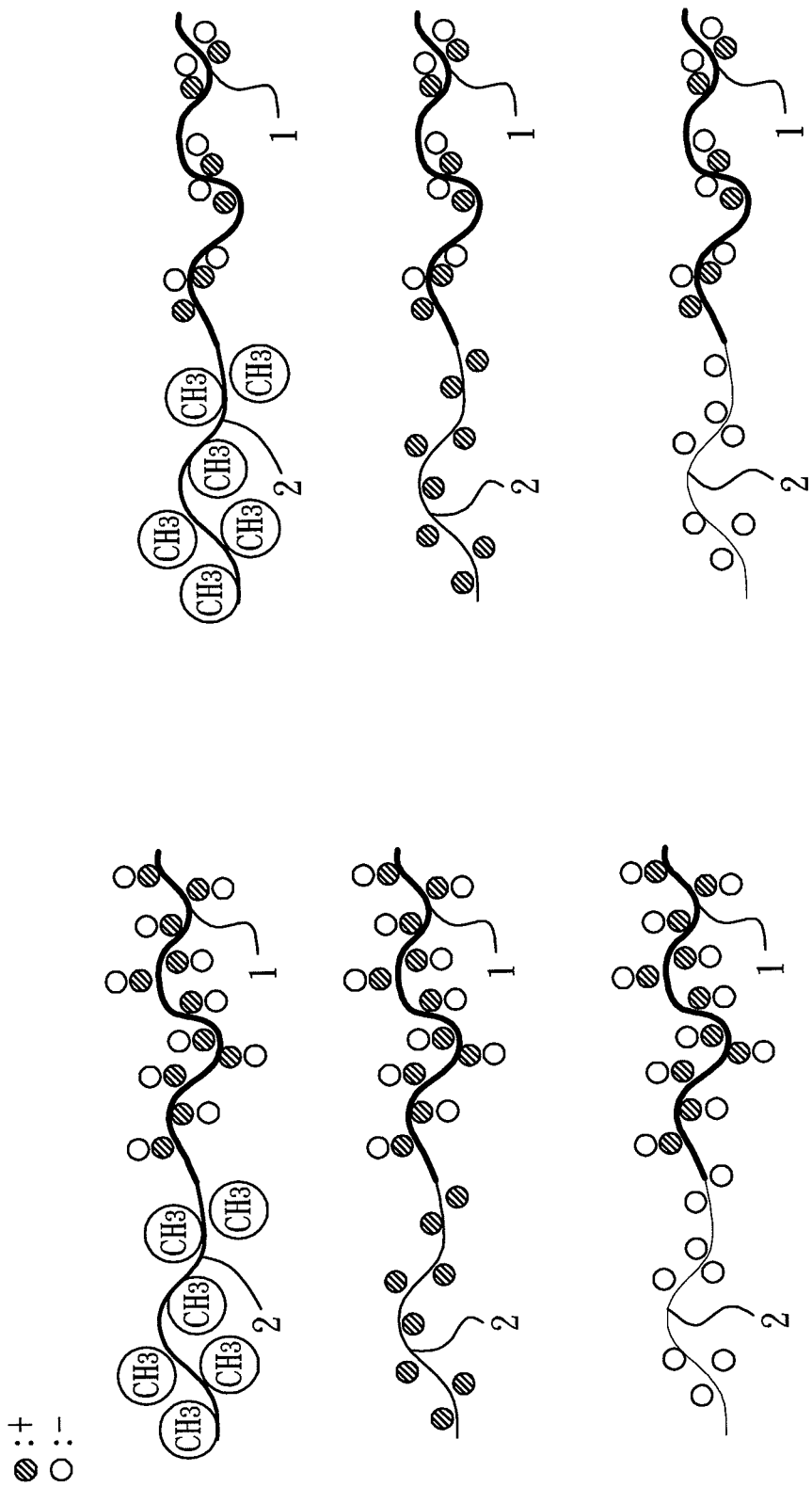
FIG. 1A and FIG. 1B illustrate some biomolecule resistance diblock copolymers employed by the surface anti-biomolecule agents of this invention.

FIG. 1A and FIG. 1B illustrate some biomolecule resistance block copolymers employed by the surface anti-biomolecule agents of this invention, wherein all copolymers are diblock copolymers consisting of a zwitterionic block 1 and an anchoring block 2, and the copolymers shown in the two figures are different in that the zwitterionic blocks 1 of FIG. 1A consist of zwitterionic monomers, and the zwitterionic blocks 1 of FIG. 1B consist of zwitterionic units comprising mix-charged monomers, which comprise mixing two oppositely charged compounds with overall charge neutrality. The anchoring block 2 may be positively or negatively charged or consists of hydrophobic groups (e.g. $CH_3$). The diblock copolymers with positively charged anchoring block are employed for treating negatively charged sites of the substrate, and vice versa. The diblock copolymers with hydrophobic anchoring block are employed for treating hydrophobic sites of the substrate.

Figure 2A:
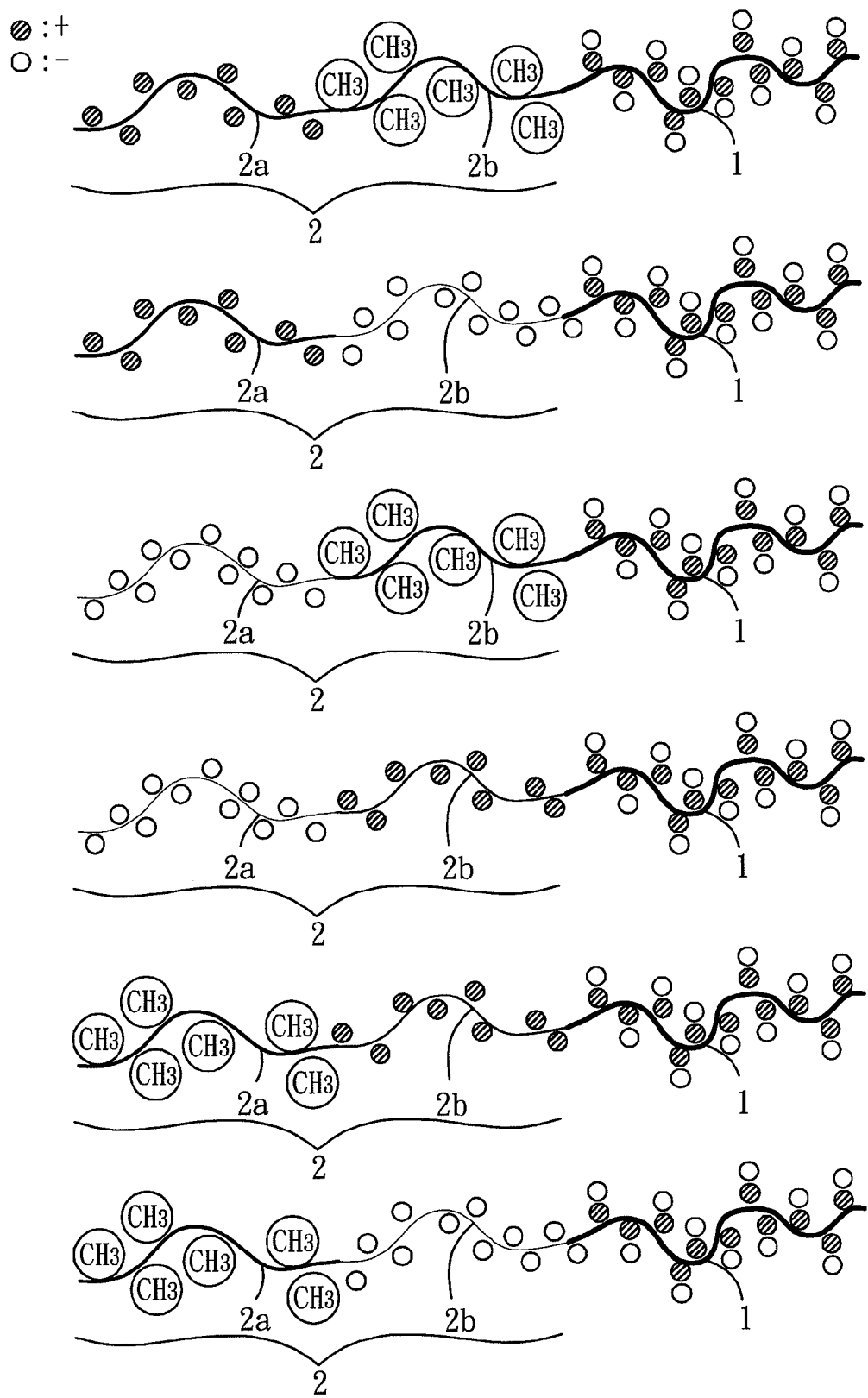
FIG. 2A and FIG. 2B illustrate some biomolecule resistance triblock copolymers employed by the surface anti-biomolecule agents of this invention.
Figure 2B:
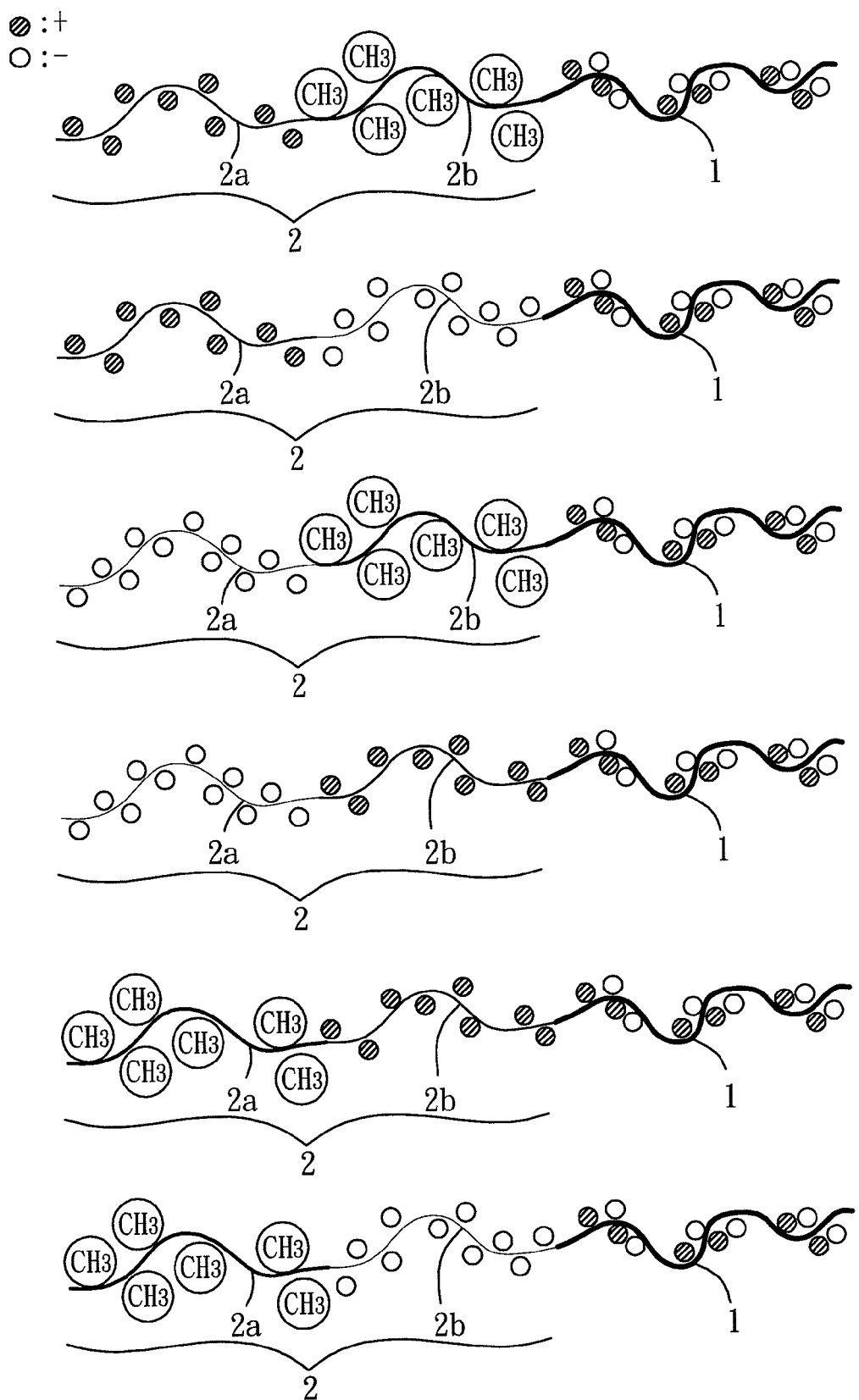

FIG. 2A and FIG. 2B illustrate some biomolecule resistance block copolymers employed by the surface anti-biomolecule agents of this invention, wherein all copolymers are triblock copolymers consisting of a zwitterionic block 1 and an anchoring block 2 with two series-connected sub-blocks 2a/2b. The copolymers shown in the two figures are different in that the zwitterionic blocks 1 of FIG. 2A consist of zwitterionic monomers, and the zwitterionic blocks 1 of FIG. 2B consist of zwitterionic units comprising mix-charged monomers. The anchoring sub-blocks 2a/2b may be positively or negatively charged or may consist of hydrophobic groups (e.g. $CH_3$). The triblock copolymers with positively charged anchoring sub-block are employed for treating negatively charged sites of the substrate, and vice versa. The triblock copolymers with hydrophobic anchoring sub-block (e.g. $CH_3$) are employed for treating hydrophobic sites of the substrate.

Figure 3A:
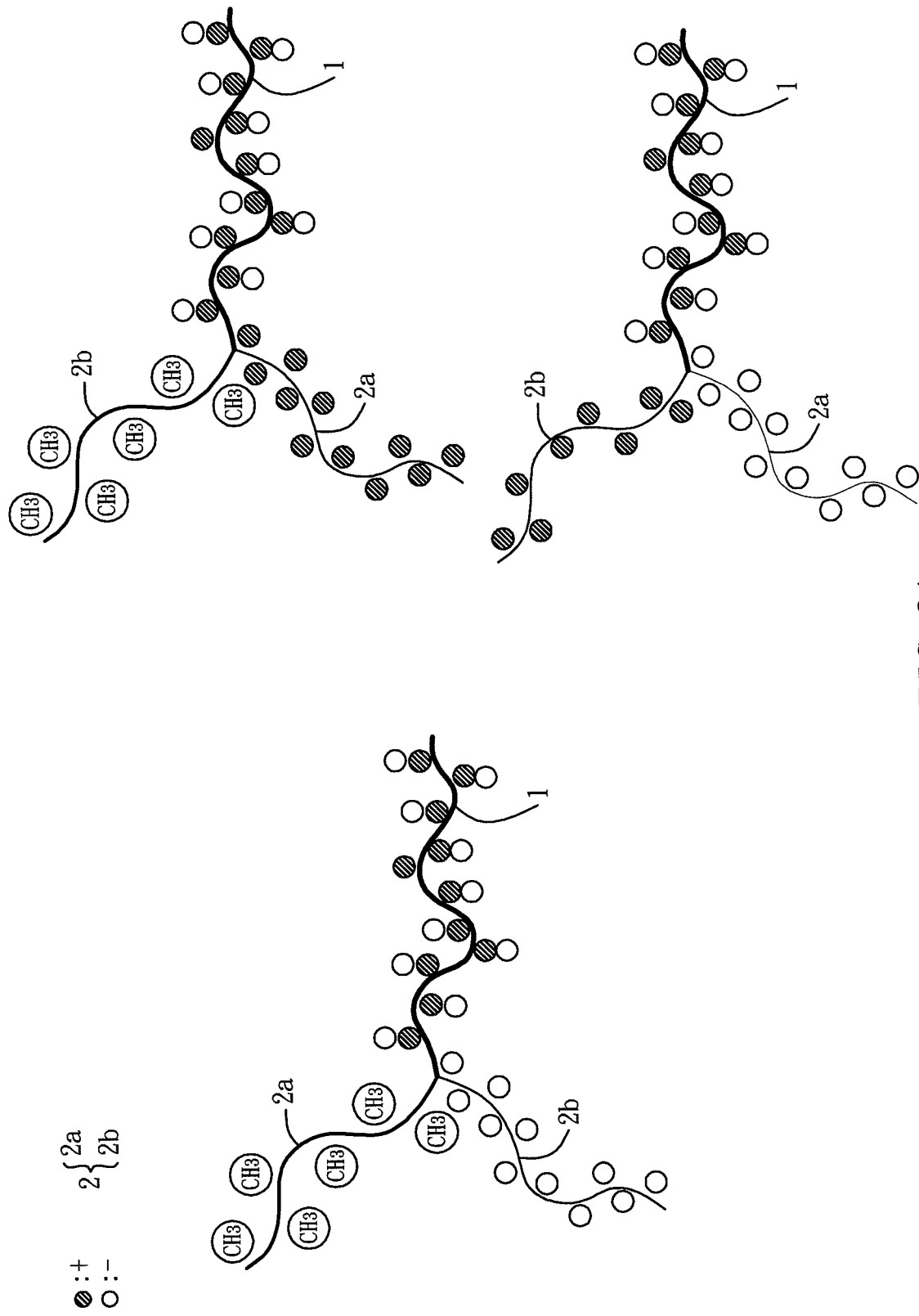
FIG. 3A and FIG. 3B illustrate some biomolecule resistance star block copolymers employed by the surface anti-biomolecule agents of this invention.
Figure 3B:
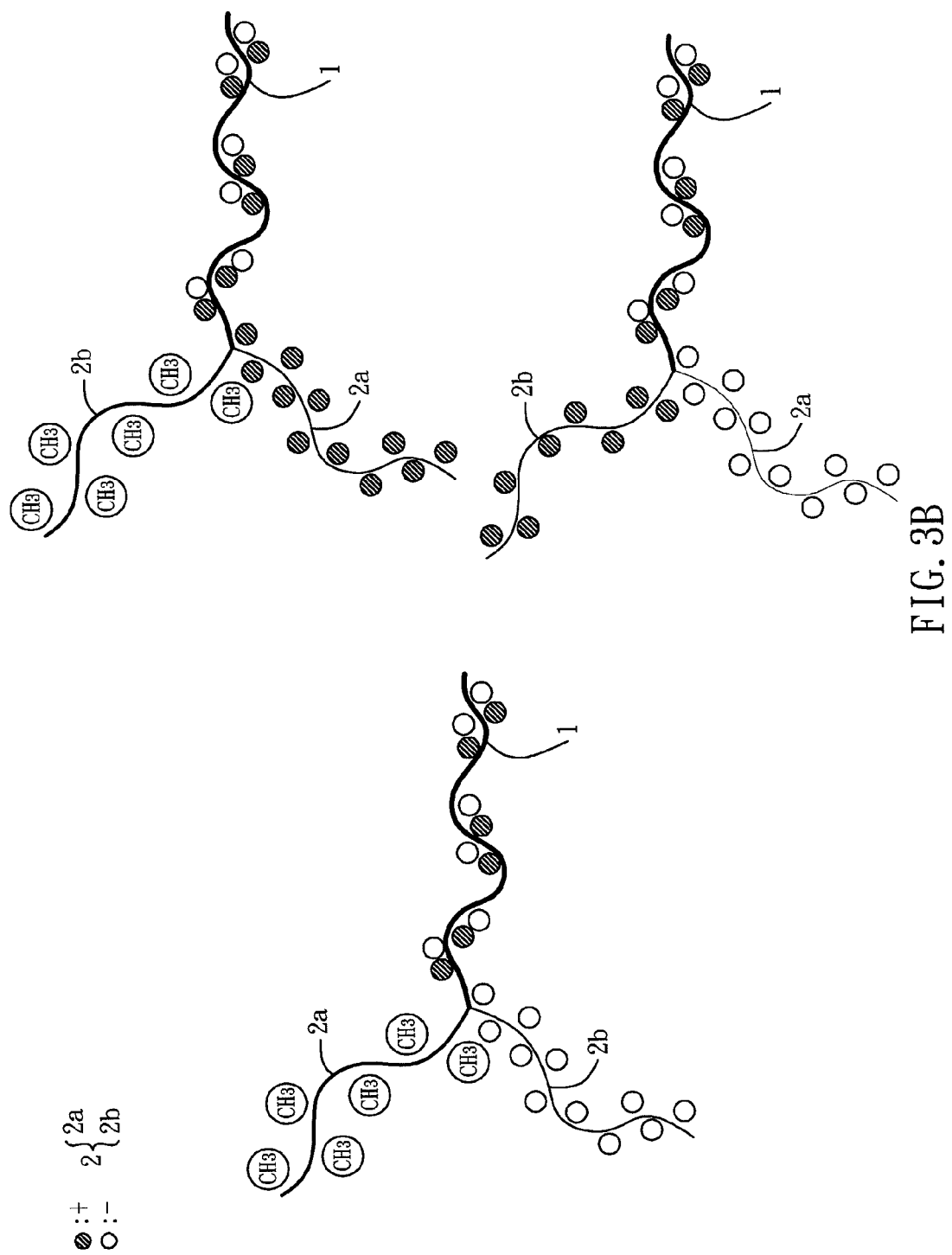

FIG. 3A and FIG. 3B illustrate some biomolecule resistance block copolymers employed by the surface anti-biomolecule agents of this invention, wherein all copolymers are star triblock copolymers consisting of a zwitterionic block 1 and two anchoring sub-blocks 2a/2b, and the copolymers shown in two figures are different in that the zwitterionic blocks 1 of FIG. 3A consist of zwitterionic monomers, and the zwitterionic blocks 1 of FIG. 3B consist of zwitterionic units comprising mix-charged monomers. The anchoring sub-block 2a/2b may be positively or negatively charged or may be a hydrophobic sub-block consisting of hydrophobic groups (e.g. $CH_3$). The star triblock copolymers with positively charged anchoring sub-block are employed for treating negatively charged sites of the substrate, and vice versa. The triblock copolymers with hydrophobic anchoring sub-block are employed for treating hydrophobic sites of the substrate.

Figure 4A:
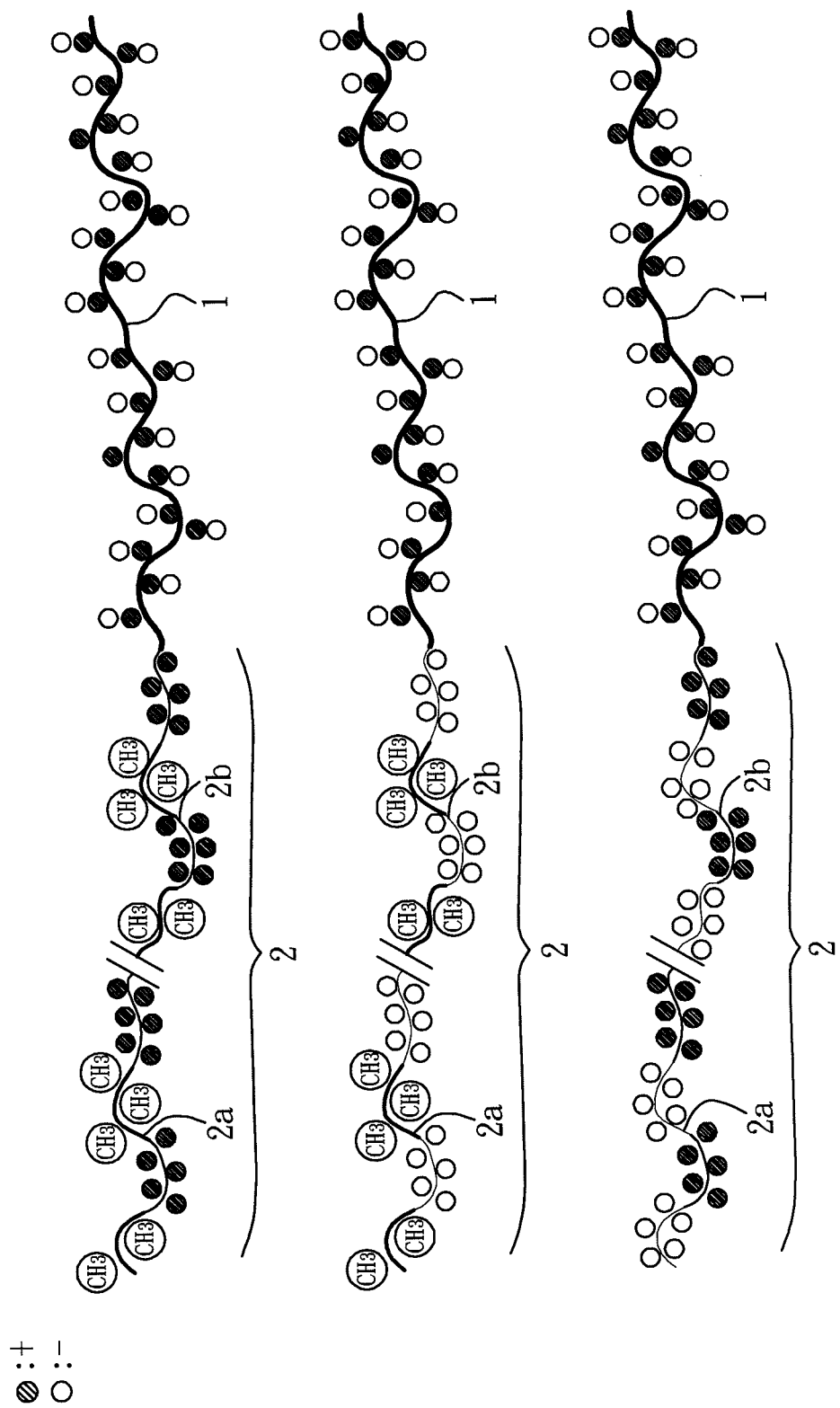
FIG. 4A and FIG. 4B illustrate some biomolecule resistance multi block copolymers employed by the surface anti-biomolecule agents of this invention.
Figure 4B:
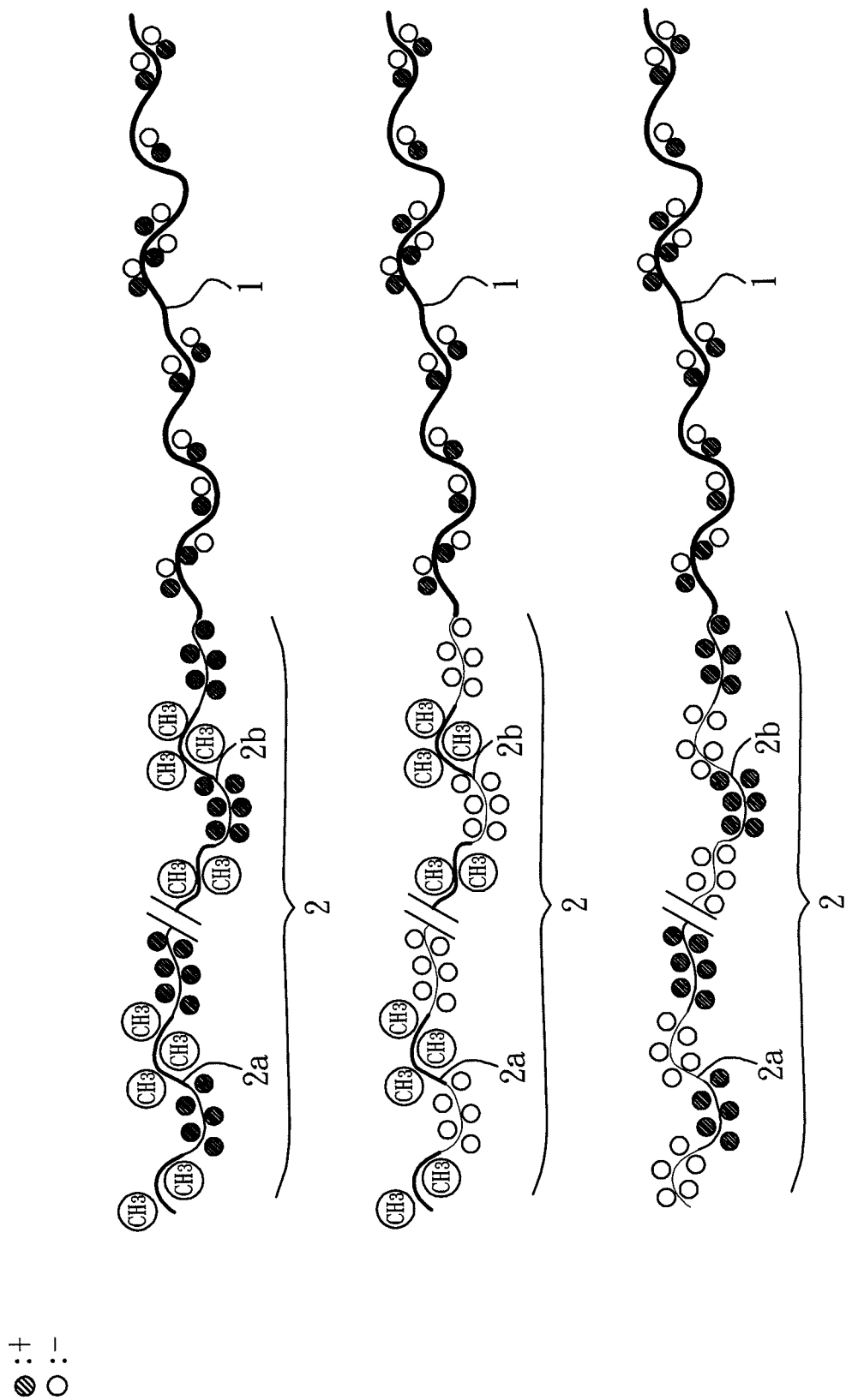

FIG. 4A and FIG. 4B illustrate some biomolecule resistance block copolymers employed by the surface anti-biomolecule agents of this invention, wherein all copolymers are multiblock copolymers consisting of a zwitterionic block 1 and an anchoring block 2 consisting of series-connected sub-blocks 2a/2b, and the copolymers shown in two figures are different in that the zwitterionic blocks 1 of FIG. 4A consist of zwitterionic monomers, and the zwitterionic blocks 1 of FIG. 4B consist of zwitterionic units comprising mix-charged monomers. The anchoring sub-block 2a/2b may be positively or negatively charged or may be a hydrophobic sub-block consisting of hydrophobic groups (e.g. $CH_3$). The multiblock copolymers with positively charged anchoring sub-block are employed for treating negatively charged sites of the substrate, and vice versa. The multiblock copolymers with hydrophobic anchoring sub-block are employed for treating hydrophobic sites of the substrate.

EXAMPLES

Table 1 lists characteristics of nine prepared biomolecule resistance diblock copolymers, according to embodiments of the present invention. The nine prepared copolymers are divided into three groups: (1) block copolymer with a zwitterionic block and an anchoring hydrophobic block (as the anchoring block), as poly(propylene oxide)-block-poly(sulfobetaine methacrylate) (PPO-b-PSBMA); (2) block copolymer with a zwitterionic block and a positively-charged anchoring block, as poly((3-methacryloyloxy)propyl)-N,N,N-trimethylammonium chloride)-block-poly(sulfobetaine methacrylate); (3) block copolymer with a zwitterionic block and a negatively-charged anchoring block, as potassium salt of poly((3-methacryloyloxy)propyl) sulfonic acid)-block-poly(sulfobetaine methacrylate) (PSA-b-PSBMA). The nine copolymers were synthesized, but not limited, using atom transfer radical polymerization (ATRP) and variant repeated units of the zwitterionic block and the anchoring block.

TABLE 1

| Sample ID | Characterization of copolymers | | | | | | Average number of repeated units | | Zeta potential | Hydrodynamic size |
| --- | --- | --- | --- | --- | --- | --- | --- | --- | --- | --- |
| | $M_w$ | $M_w/M_n$ | $M_w$ of poly | $M_w$ of polySBMA | polySBMA content | | | | | |
| | (g/mol) | | | | (wt %) | (mol %) | m | n | 1 mg/ml | 1 mg/ml |
| PPO$_{20}$-b-PSBMA$_{10}$ | 3952 | 1.267 | 1057 | 2895 | 73.3 | 33.3 | 20 | 10 | −0.2 | ~10 |
| PPO$_{20}$-b-PSBMA$_{20}$ | 6038 | 1.217 | 1057 | 4981 | 82.5 | 47.4 | 20 | 18 | −0.5 | ~10 |
| PPO$_{20}$-b-PSBMA$_{40}$ | 12775 | 1.236 | 1057 | 11718 | 91.7 | 67.7 | 20 | 42 | +0.7 | ~11 |
| PTMA$_{20}$-b-PSBMA$_{10}$ | 7765 | 1.214 | 4596 | 3169 | 40.8 | 33.3 | 22 | 11 | +1.4 | ~10 |
| PTMA$_{20}$-b-PSBMA$_{20}$ | 10176 | 1.435 | 4596 | 5592 | 55.0 | 47.6 | 22 | 20 | +3.2 | ~10 |
| PTMA$_{20}$-b-PSBMA$_{40}$ | 16158 | 1.312 | 4596 | 11562 | 71.6 | 65.1 | 22 | 41 | +4.3 | ~13 |
| PSA$_{20}$-b-PSBMA$_{10}$ | 7750 | 1.207 | 5060 | 2690 | 34.7 | 32.3 | 21 | 10 | −0.9 | ~10 |
| PSA$_{20}$-b-PSBMA$_{20}$ | 10620 | 1.346 | 5060 | 5660 | 53.3 | 48.8 | 21 | 20 | −2.8 | ~11 |
| PSA$_{20}$-b-PSBMA$_{40}$ | 15202 | 1.287 | 5060 | 10142 | 66.7 | 63.2 | 21 | 36 | −3.7 | ~12 |

Another embodiment of this invention provides a surface anti-biomolecule agent used in an artificially or naturally charged substrate. The surface anti-biomolecule agent comprises preferably equal to or more than 0.1 mg/ml of a biomolecule resistance random copolymer, which comprises a zwitterionic domain and an anchoring domain consisting of at least a sub-domain having a first electricity, wherein the sub-domain having the first electricity binds to sites of the charged substrate having a second electricity opposite to the first electricity, and the zwitterionic domain extends outwardly to reduce the attachment of biomolecules to the charged substrate.

The anchoring domain may further comprise at least a sub-domain having the second electricity, so as to bind to sites of the charged substrate having the first electricity. In this case, both of the anchoring domain and the charged substrate have the first electricity and the second electricity, and the ratio of the number of the sub-domain having the first electricity to the number of the sub-domain having the second electricity is related to the ratio of the number of the sites having the second electricity to the number of the sites having the first electricity.

In addition, the charged substrate may further comprise hydrophobic sites. In this case, the anchoring domain further comprises at least a sub-domain consisting of hydrophobic groups, so as to bind to hydrophobic sites of the charged substrate via hydrophobic interactions. And similarly, the number ratio of the sub-domain having the first electricity to the sub-block having hydrophobic groups is related to the number ratio of the sites having the second electricity to the hydrophobic sites.

In this embodiment, the first electricity may be positive electricity or negative electricity.

Preferably, the zwitterionic domain is polymerized by a zwitterionic monomer selected from the group consisting of sulfobetaine, carboxylbetaine, derivatives thereof, and combinations thereof. Alternatively, the zwitterionic domain may be polymerized by a zwitterionic unit comprising mix-charged monomers, and the mix-charged monomers comprise mixing two oppositely charged compounds with overall charge neutrality.

Figure 5A:
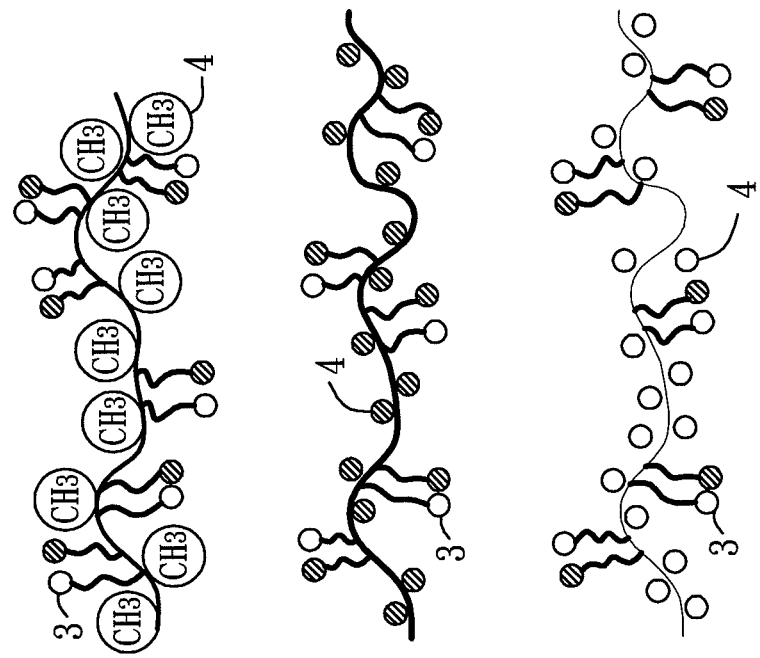
FIG. 5A and FIG. 5B illustrate some biomolecule resistance random copolymers employed by the surface anti-biomolecule agents of this invention.
Figure 5B:
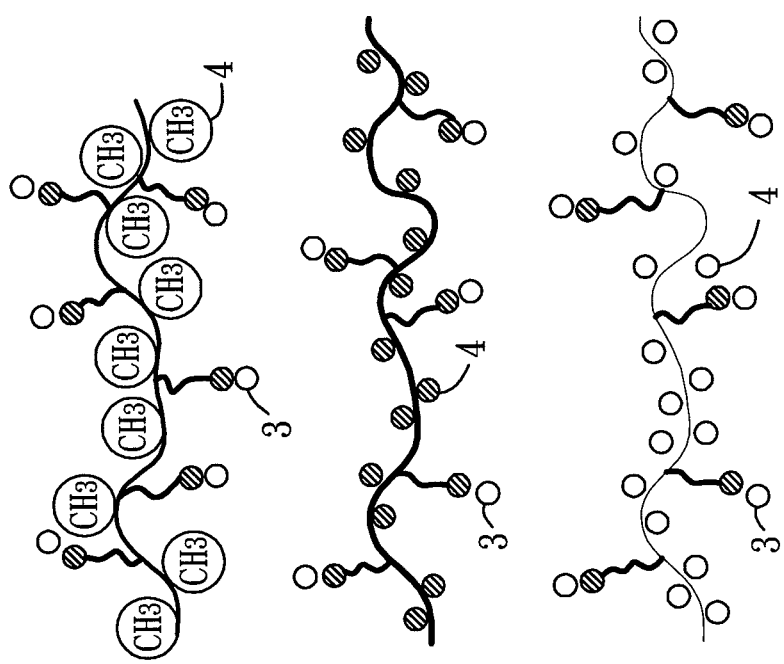

FIG. 5A and FIG. 5B illustrate some biomolecule resistance random copolymers employed by the surface anti-biomolecule agents of this invention, wherein all copolymers are random copolymers consisting of a zwitterionic domain 3 and an anchoring domain 4, and the copolymers shown in the two figures are different in that the zwitterionic domains 3 of FIG. 5A consist of zwitterionic monomers, and the zwitterionic domains 3 of FIG. 5B consist of zwitterionic units comprising mix-charged monomers. The anchoring domain 4 may be positively or negatively charged or consist of hydrophobic pendant groups (e.g. CH$_3$). The random copolymers with positively charged anchoring domain are employed for treating negatively charged sites of the substrate, and vice versa. The random copolymers with hydrophobic anchoring domain are employed for treating hydrophobic sites of the substrate.

Figure 6A:
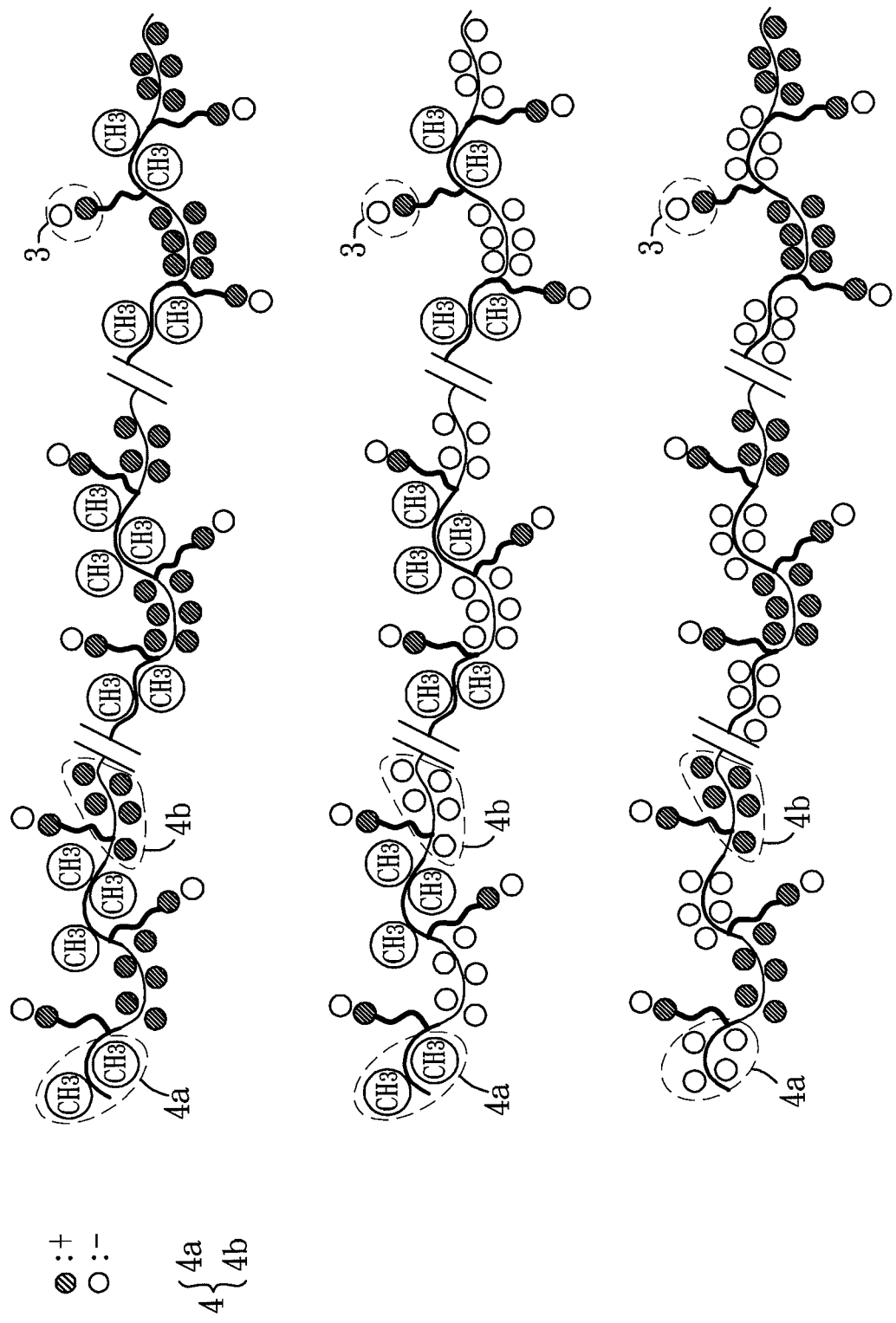
FIG. 6A and FIG. 6B illustrate some biomolecule resistance multi random copolymers employed by the surface anti-biomolecule agents of this invention.
Figure 6B:
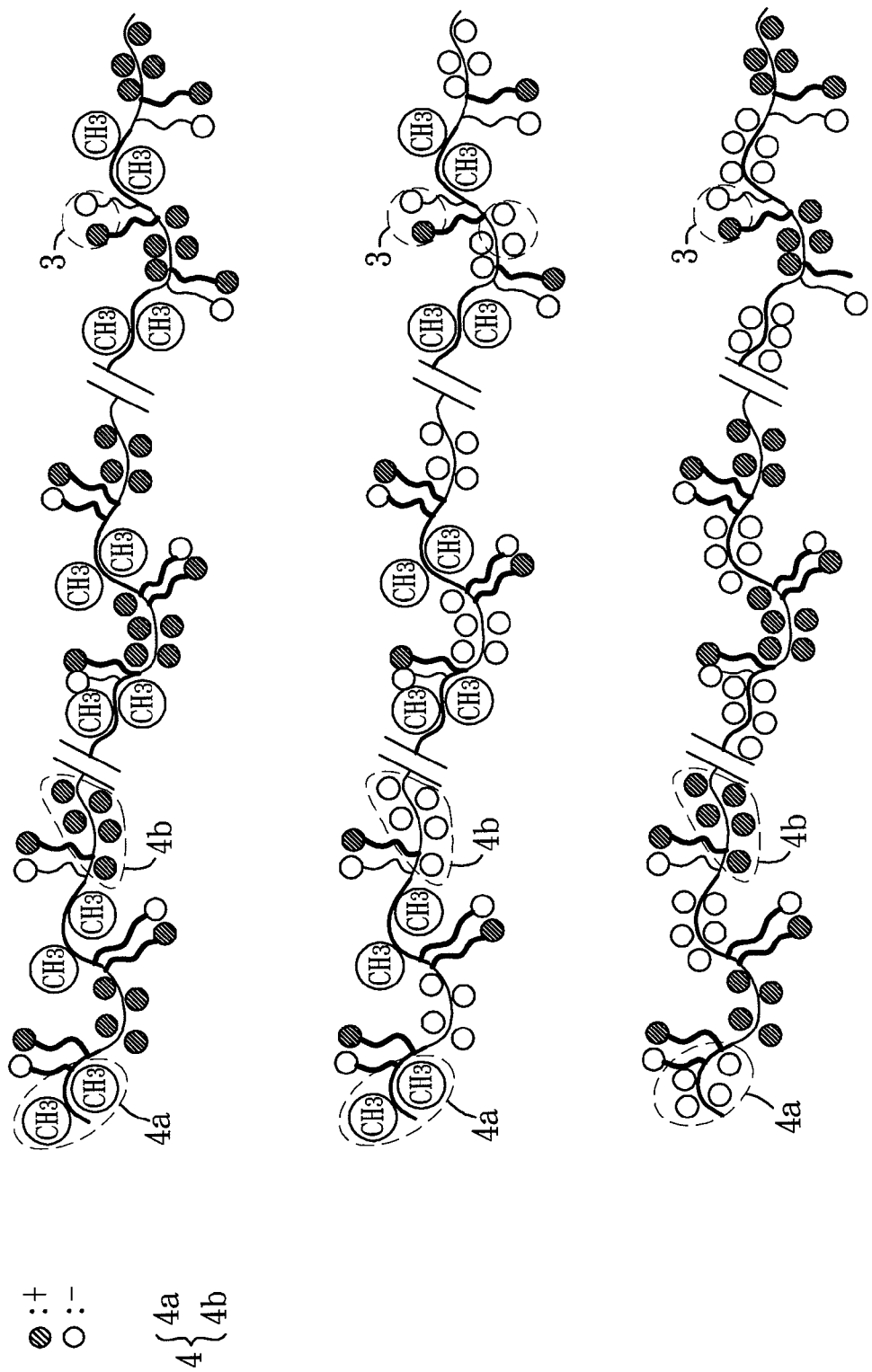

FIG. 6A and FIG. 6B illustrate some biomolecule resistance random copolymers employed by the surface anti-biomolecule agents of this invention, wherein all copolymers are multirandom copolymers consisting of a zwitterionic domain 3 and an anchoring domain 4 consisting of many series-connected sub-domains 4a/4b, and the copolymers shown in the two figures are different in that the zwitterionic domains 3 of FIG. 6A consist of zwitterionic monomers, and the zwitterionic domains 3 of FIG. 6B consist of zwitterionic units comprising mix-charged monomers. The anchoring sub-domain 4a/4b may be positively or negatively charged or may consist of hydrophobic pendant groups (e.g. CH$_3$). The multirandom copolymers with positively charged anchoring sub-domain are employed for treating negatively charged sites of the substrate, and vice versa. The multirandom copolymers with hydrophobic anchoring sub-domain are employed for treating hydrophobic sites of the substrate.

Another embodiment of this invention provides a surface anti-biomolecule agent for an artificially or naturally charged substrate. The surface anti-biomolecule agent comprises preferably equal to or more than 0.1 mg/ml of a biomolecule resistance copolymer, which comprises a anchoring main chain and a zwitterionic pendant group or zwitterionic side chain, the anchoring main chain having a sub-block or a sub-domain with a first electricity, wherein the sub-block or the sub-domain having the first electricity binds to sites of the charged substrate having a second electricity opposite to the first electricity, and the zwitterionic pendant group or zwitterionic side chain extends outwardly to reduce the attachment of biomolecules to the charged substrate.

The anchoring main chain may further comprise a sub-block or sub-domain having the second electricity, so as to bind to sites of the charged substrate having the first electricity.

The anchoring domain further comprises a sub-block or sub-domain having hydrophobic groups, so as to bind to hydrophobic sites of the charged substrate.

The anchoring main chain may be homo polymer, block copolymer or random copolymer. The first electricity is positive electricity or negative electricity.

Preferably, the zwitterionic pendant group or zwitterionic side chain is polymerized by a zwitterionic monomer selected from the group consisting of sulfobetaine, carboxylbetaine, derivatives thereof, and combinations thereof. Alternatively, the zwitterionic pendant group or zwitterionic side chain is polymerized by a zwitterionic unit comprising mix-charged monomers, and the mix-charged monomers comprise mixing two oppositely charged compounds with overall charge neutrality.

Figure 7A:
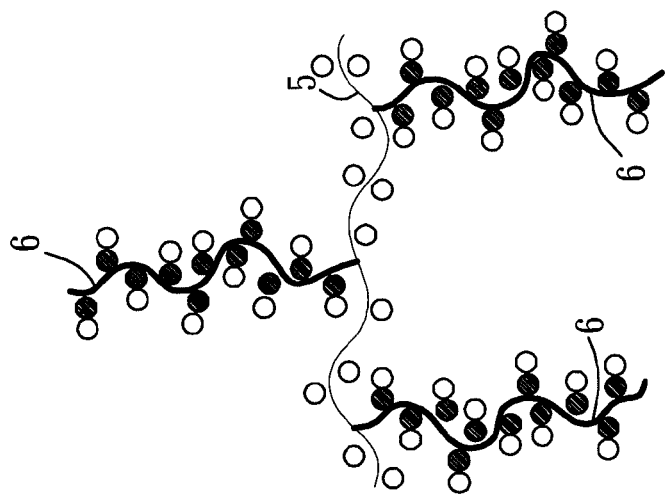
FIG. 7A and FIG. 7B illustrate some biomolecule resistance copolymers with anchoring main chain and one or more zwitterionic side chains employed by the surface anti-biomolecule agents of this invention.
Figure 7A:
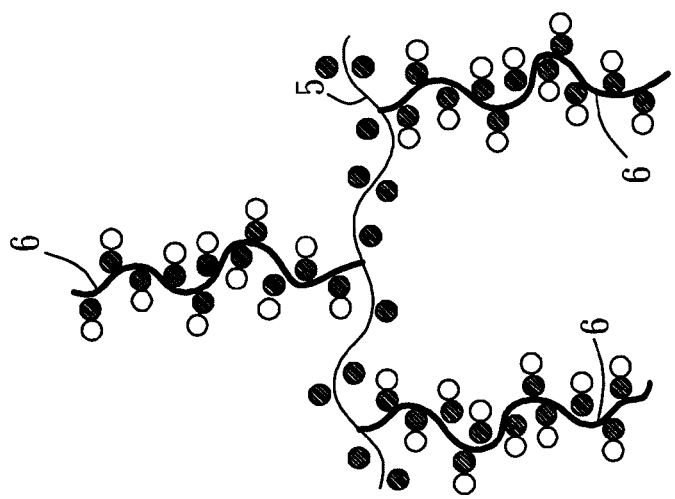
Figure 7A:
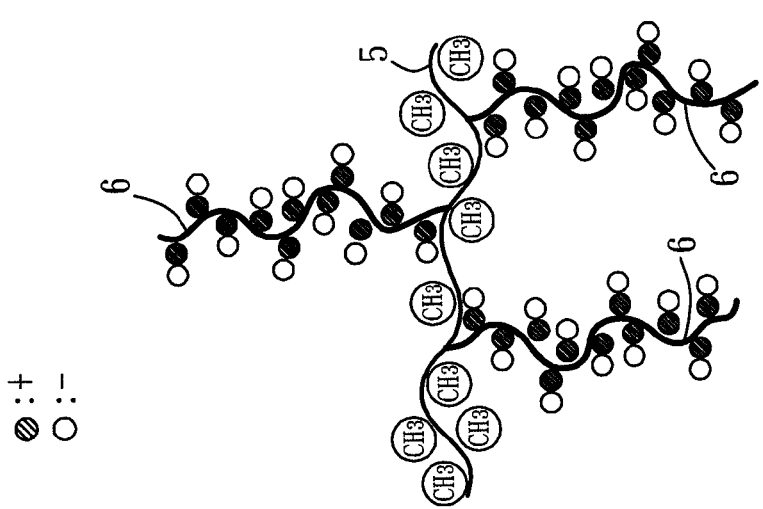
Figure 7B:
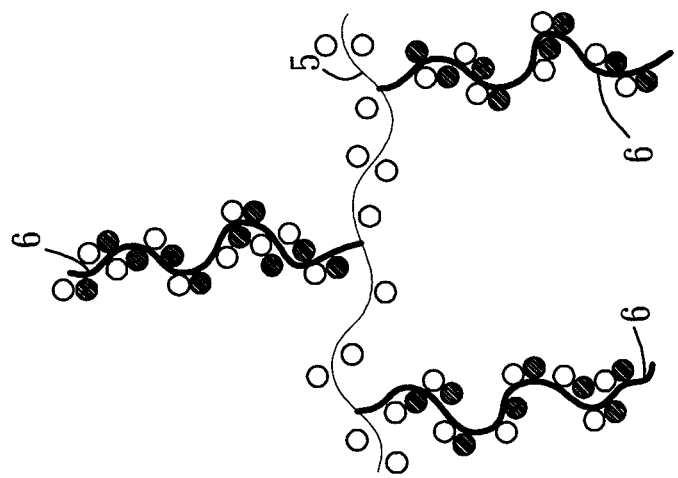
Figure 7B:
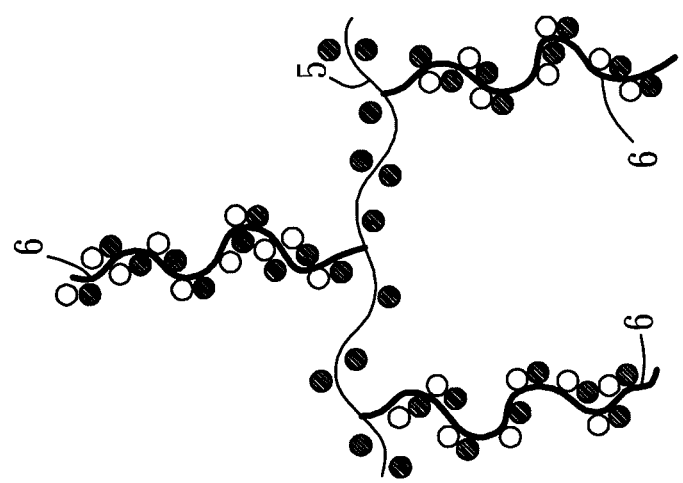
Figure 7B:
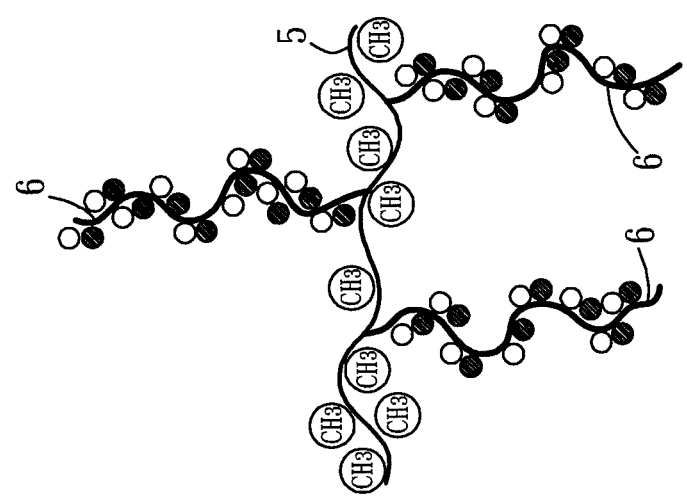

FIG. 7A and FIG. 7B illustrate some biomolecule resistance copolymers employed by the surface anti-biomolecule agents of this invention, wherein all copolymers consist of an anchoring main chain 5 and one or more zwitterionic side chains 6, and the copolymers shown in the two figures are different in that the zwitterionic side chains 6 of FIG. 7A consist of zwitterionic monomers, and the zwitterionic side chains 6 of FIG. 7B consist of zwitterionic units comprising mix-charged monomers. The anchoring main chain 5 may be positively or negatively charged or may consist of hydrophobic pendant groups (e.g. $CH_3$). The copolymers with positively charged anchoring main chain are employed for treating negatively charged sites of the substrate, and vice versa. The copolymers with hydrophobic anchoring main chain are employed for treating hydrophobic sites of the substrate.

Figure 7C:
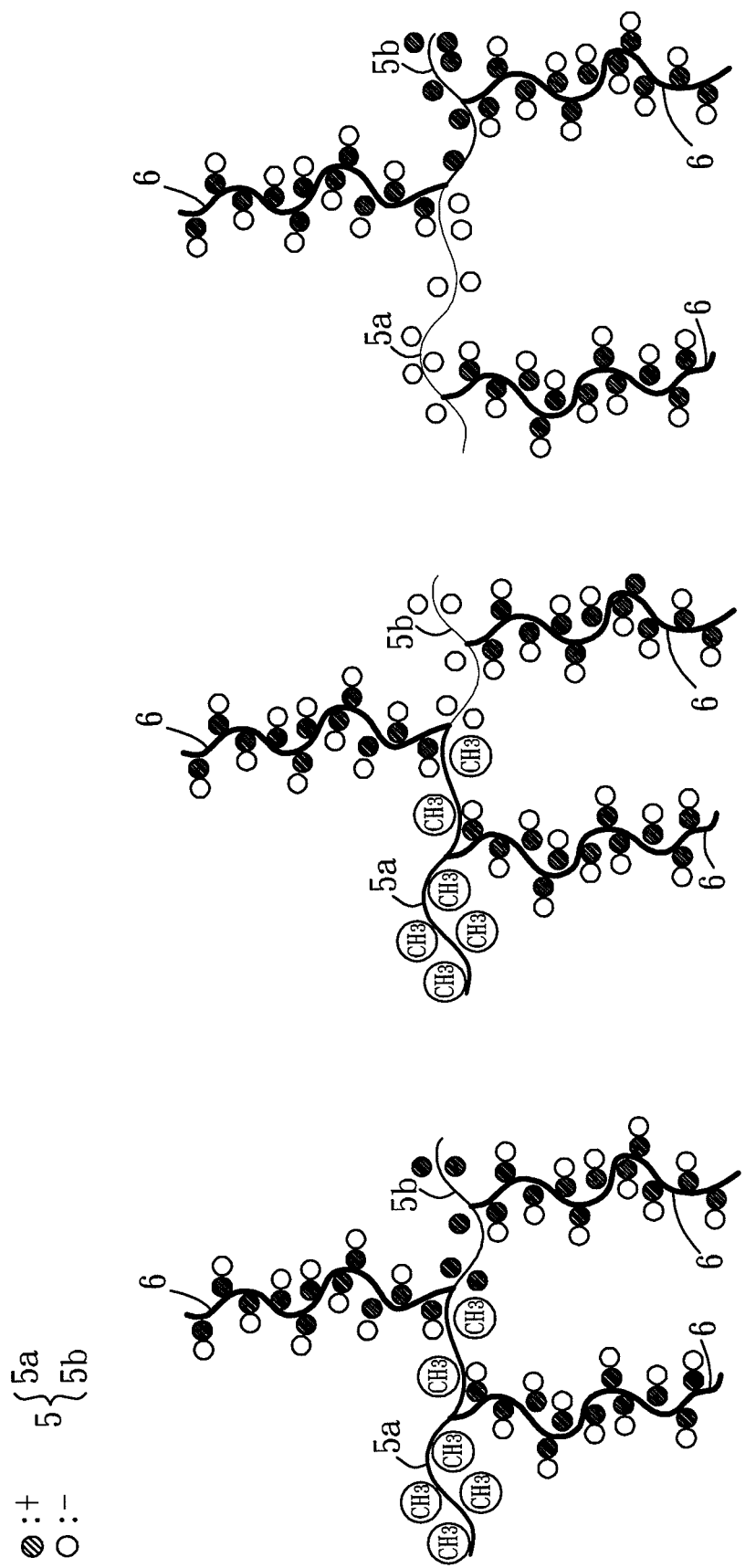
FIG. 7C and FIG. 7D illustrate some biomolecule resistance copolymers with anchoring main chain consisting of sub-blocks and one or more zwitterionic side chains employed by the surface anti-biomolecule agents of this invention.
Figure 7D:
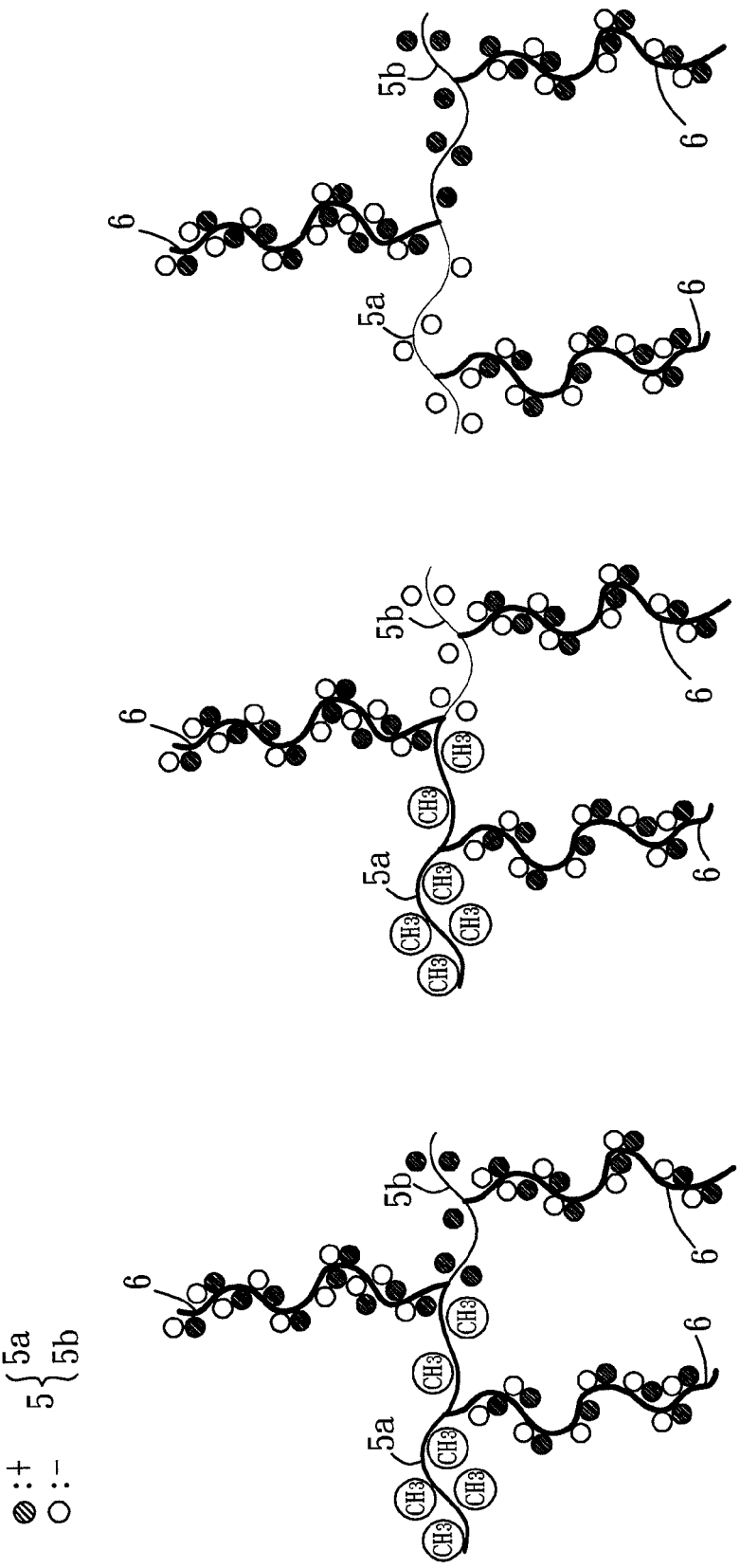

FIG. 7C and FIG. 7D illustrate some biomolecule resistance copolymers employed by the surface anti-biomolecule agents of this invention, wherein all copolymers consist of an anchoring main chain 5 consisting of sub-blocks 5a/5b and one or more zwitterionic side chains 6, and the copolymers shown in the two figures are different in that the zwitterionic side chains 6 of FIG. 7C consist of zwitterionic monomers, and the zwitterionic side chains 6 of FIG. 7D consist of zwitterionic units comprising mix-charged monomers. The anchoring sub-blocks 5a/5b may be positively or negatively charged or may consist of hydrophobic pendant groups (e.g. $CH_3$). The copolymers with positively charged anchoring sub-block are employed for treating negatively charged sites of a substrate, and vice versa. The copolymers with hydrophobic anchoring sub-block are employed for treating hydrophobic sites of the substrate.

Figure 7E:
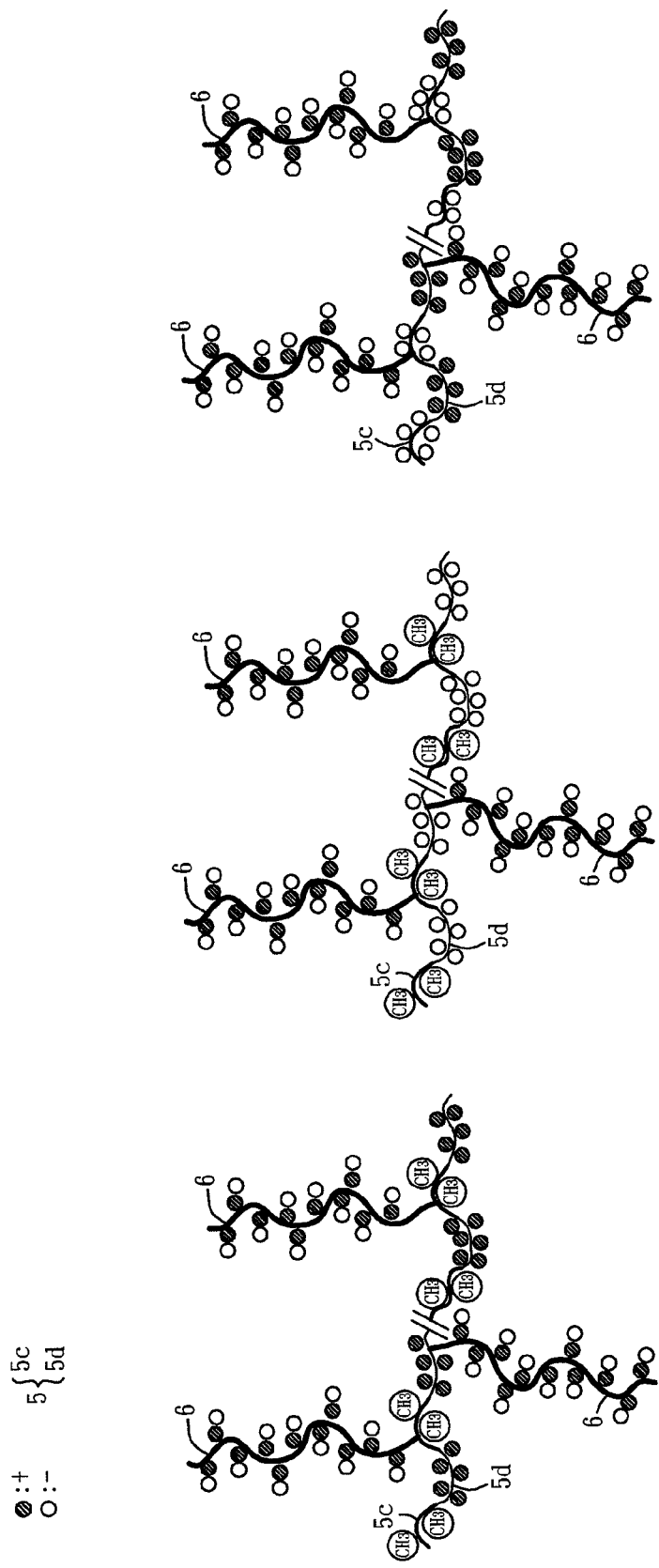
FIG. 7E and FIG. 7F illustrate some biomolecule resistance copolymers with anchoring main chain consisting of series-connected sub-domains and one or more zwitterionic side chains, employed by the surface anti-biomolecule agents of this invention.
Figure 7F:
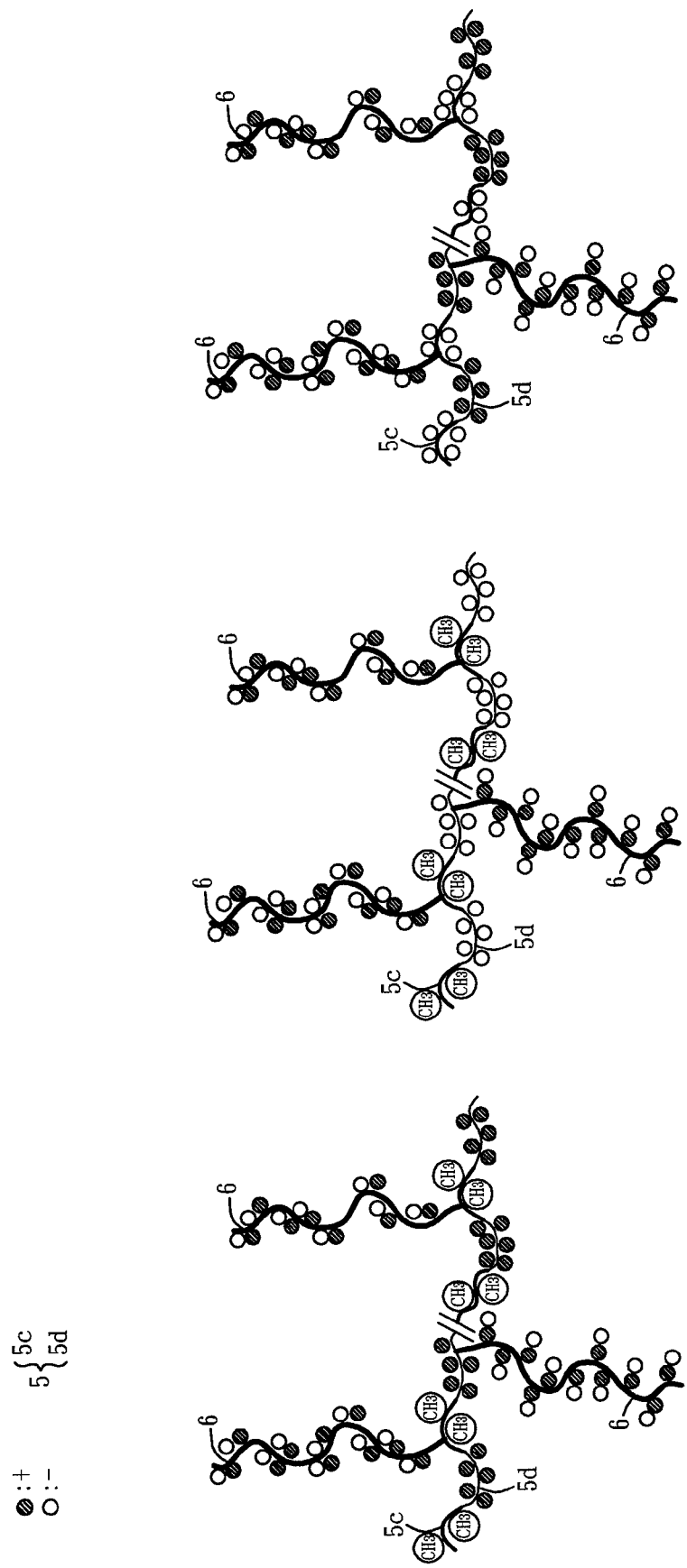

FIG. 7E and FIG. 7F illustrate some biomolecule resistance copolymers employed by the surface anti-biomolecule agents of this invention, wherein all copolymers consist of an anchoring main chain 5 consisting of series-connected sub-domains 5c/5d and one or more zwitterionic side chains 6, and the copolymers shown in the two figures are different in that the zwitterionic side chains 6 of FIG. 7E consist of zwitterionic monomers, and the zwitterionic side chains 6 of FIG. 7F consist of zwitterionic units comprising mix-charged monomers. The anchoring sub-domain 5c/5d may be positively or negatively charged or may consist of hydrophobic pendant groups (e.g. $CH_3$). The copolymers with positively charged anchoring sub-domains are employed for treating negatively charged sites of a substrate, and vice versa. The copolymers with hydrophobic anchoring sub-domains are employed for treating hydrophobic sites of the substrate.

Although specific embodiments have been illustrated and described, it will be appreciated by those skilled in the art that various modifications may be made without departing from the scope of the present invention, which is intended to be limited solely by the appended claims.

What is claimed is:

1. A surface anti-biomolecule agent for a positively charged substrate, comprising:

a zwitterionic block, extending outwardly from said positively charged substrate to reduce the attachment of biomolecules, polymerized from zwitterionic monomers selected from the group consisting of:

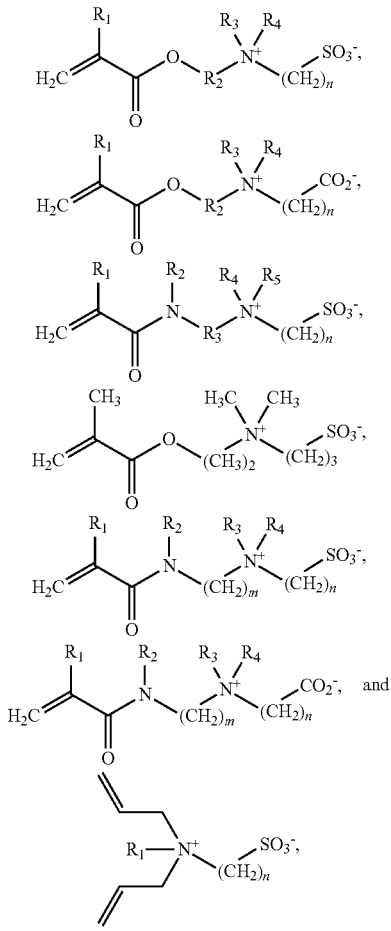

where $R_1$, $R_2$, $R_3$, $R_4$, and $R_5$ are alkyl groups, and n and m are integers of 2 to 5; and an anchoring block, being negatively charged, derived from polymerization of one moiety selected from the group consisting of:

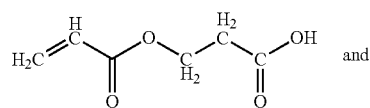

-continued

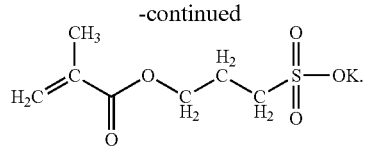

2. The surface anti-biomolecule agent as recited in claim 1, wherein the concentration of the biomolecule resistance block copolymer in the surface anti-biomolecule agent is equal to or more than 0.1 mg/ml.

3. The surface anti-biomolecule agent as recited in claim 1, wherein the copolymer is a diblock copolymer of the potassium salt of poly((2-methacryloyloxy propyl sulfonic acid)-block-poly (sulfobetaine methacrylate).

4. The surface anti-biomolecule agent as recited in claim 1, wherein the weight average molecular weight ($M_w$) of the zwitterionic block is equal to or more than 10 kDa.

5. The surface anti-biomolecule agent as recited in claim 3, wherein the average molecular weight (Mw) of the poly(sulfobetaine methacrylate) is greater than or equal to 10 kilodaltons.

6. The surface anti-biomolecule agent as recited in claim 3, wherein the average number of repeated units of the potassium salt of poly((2-(methacryloyloxy)propyl)-sulfonic acid) is 21, and the average number of repeated units of the poly (sulfobetaine methacrylate) is 20.

7. The surface anti-biomolecule agent as recited in claim 3, wherein the concentration of the diblock copolymer of potassium salt of poly((2-(methacryloyloxy)propyl)-sulfonic acid)-block-poly(sulfobetaine methacrylate)in the surface anti-biomolecule agent is equal to or more than 0.1 mg/ml.

* * * * *